(12) United States Patent
Lenarz et al.

(10) Patent No.: US 7,742,827 B2
(45) Date of Patent: Jun. 22, 2010

(54) PATTERNING OF THE SURFACE OF IMPLANTABLE DEVICES FOR TISSUE GROWTH MANAGEMENT

(75) Inventors: Thomas Lenarz, Hannover (DE); John L. Parker, Roseville (AU); Dusan Milojevic, Westleigh (AU)

(73) Assignee: Cochlear Limited, Lane Cove, New South Wales (AU)

( * ) Notice: Subject to any disclaimer, the term of this patent is extended or adjusted under 35 U.S.C. 154(b) by 1192 days.

(21) Appl. No.: 11/159,255

(22) Filed: Jun. 23, 2005

(65) Prior Publication Data

US 2006/0020318 A1    Jan. 26, 2006

(30) Foreign Application Priority Data

Jun. 23, 2004    (AU) ............................. 2004903436

(51) Int. Cl.
*A61N 1/18*    (2006.01)

(52) U.S. Cl. ............................ 607/137; 607/45; 607/57
(58) Field of Classification Search ................. 607/115, 607/116, 137, 45, 122, 55
See application file for complete search history.

(56) References Cited

U.S. PATENT DOCUMENTS

| 5,651,767 A | * | 7/1997 | Schulman et al. | ............. 604/8 |
| 6,205,359 B1 | * | 3/2001 | Boveja | .................. 607/45 |
| 6,304,787 B1 | * | 10/2001 | Kuzma et al. | ............. 607/137 |
| 6,374,143 B1 | * | 4/2002 | Berrang et al. | ............ 607/137 |

* cited by examiner

*Primary Examiner*—Carl H. Layno
*Assistant Examiner*—Jon-Eric C. Morales
(74) *Attorney, Agent, or Firm*—Connolly Bove Lodge & Hutz LLP (57) ABSTRACT

An implantable tissue-stimulating device for an implantee. The device comprising an elongate member having at least one electrode. At least a portion of the surface of the elongate member having a configuration that at least partially controls any tissue growth on and/or round the elongate member.

32 Claims, 7 Drawing Sheets

PATTERNING OF THE SURFACE OF IMPLANTABLE DEVICES FOR TISSUE GROWTH MANAGEMENT

CROSS-REFERENCE TO RELATED APPLICATIONS

This application claims the priority of co-pending Australian Patent No. 2004903436 entitled "Patterning of the Surface of Implantable Devices For Tissue Growth Management," filed Jun. 23, 2004. The entire disclosure and contents of the above application is hereby incorporated by reference herein.

BACKGROUND

1. Field of the Invention

The present application relates to an implantable apparatus, such as a hearing implant, that delivers electrical stimulation to an implantee.

2. Related Art

During insertion of an electrode array into the cochlea there is the potential for damage to be caused to the sensitive cochlear tissues. Such damage may not prevent useful safe working of the device but may result in tissue growth occurring within the cochlea following implantation.

The power consumption and efficiency of a hearing implant depends on the impedance of its electrodes. The deposition of material on the electrodes following implantation will in most instances increase that impedance. Studies have demonstrated that a build up of tissue growth occurs on and/or around electrode following implantation due to deposition of organic molecules from the perilymph within the cochlea. Tissue growth may also occur as result of an injury to the body caused by the implantation or some other interaction between the body and the implant.

Tissue growth in other circumstances may though be beneficial. For example, tissue growth is desirable to ensure closing of the cochleostomy and so creating a barrier to bacteria and viruses entering the cochlea.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable tissue-stimulating device for an implantee comprising an elongate member having at least one electrode, wherein at least a portion of the surface of the elongate member has a configuration that at least partially controls tissue growth on and/or around the elongate member.

In one embodiment, the configuration may be a pattern formed in the portion of the surface of the elongate member. The surface pattern can be adapted to direct tissue growth away from said at least one electrode following implantation. In another embodiment, the surface pattern may be adapted to enhance tissue growth in one or more particular locations. In a still further embodiment, the surface pattern may be adapted to at least partially suppress tissue growth in one or more particular locations.

According to a second aspect, the present invention is an implantable tissue-stimulating device for an implantee comprising an elongate member having at least one electrode, wherein at least a portion of the surface of the elongate member has a coating of a molecule adsorption promoting material that at least partially controls any tissue growth on and/or around the elongate member.

In one embodiment of this aspect, the molecule adsorption promoting material is myosin and is coated on the surface of the elongate material in a patterned arrangement to direct tissue growth away from the at least one electrode following implantation. In another embodiment, the patterned arrangement of the molecule adsorption promoting material may be adapted to enhance tissue growth in one or more particular locations. In a still further embodiment, the patterned arrangement of the molecule adsorption promoting material may be adapted to at least partially suppress tissue growth in one or more particular locations.

According to a third aspect, the present invention is an implantable tissue-stimulating device for an implantee comprising an elongate member having at least one electrode, at least a portion of the surface of the elongate member having a configuration that at least partially controls tissue growth on and/or around the elongate member, said portion of the surface of the elongate member further having a coating of a molecule adsorption promoting material that assists in at least partially controlling tissue growth on and/or around the elongate member.

BRIEF DESCRIPTION OF THE DRAWINGS

By way of example only, the invention is now described with reference to the accompanying drawings.

DETAILED DESCRIPTION

The power consumption and efficiency of a tissue-stimulating device, such as a Cochlear implant, depends on the impedance of the electrodes positioned on the intracochlear electrode array. Factors that are thought to increase the impedance of the electrodes include adsorption of organic molecules onto the electrodes and subsequent growth of fibrous tissue on the electrodes or on the surrounding elongate member supporting them.

Figure 1:
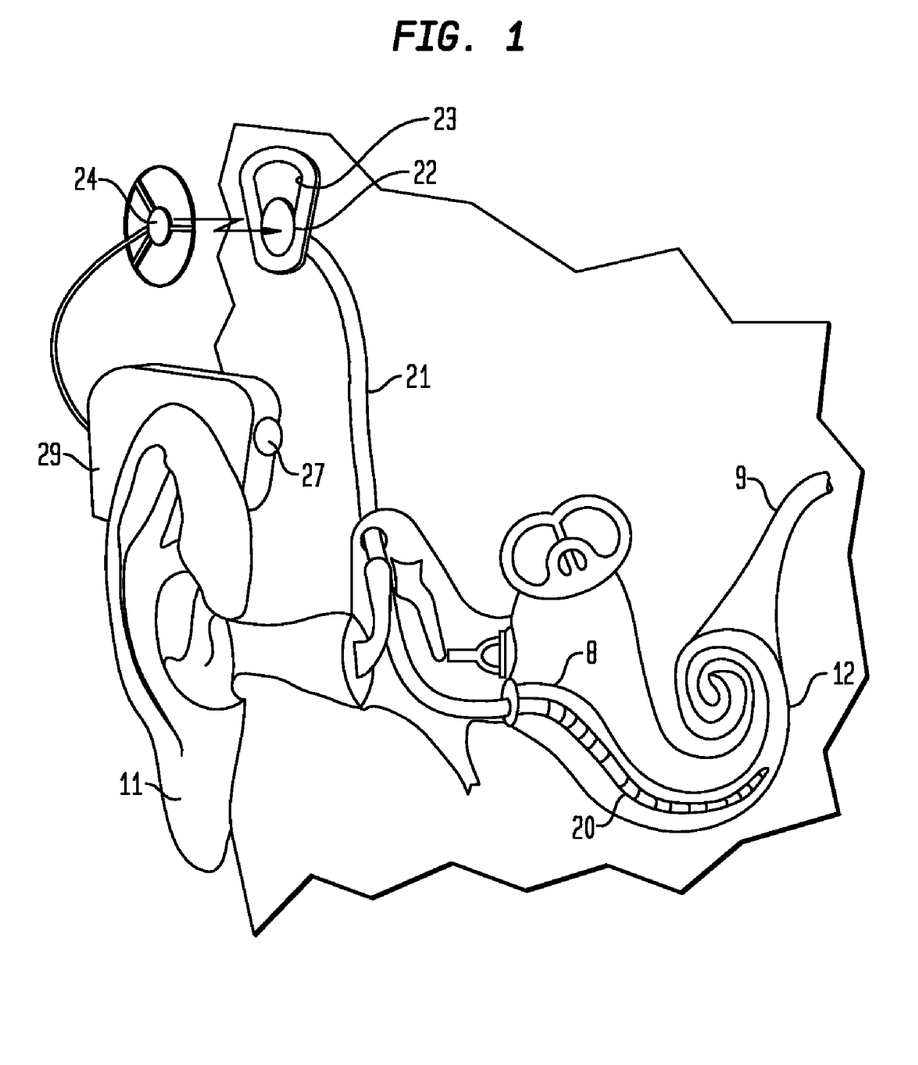
FIG. 1 is a pictorial representation of a hearing implant system.
Figure 2:
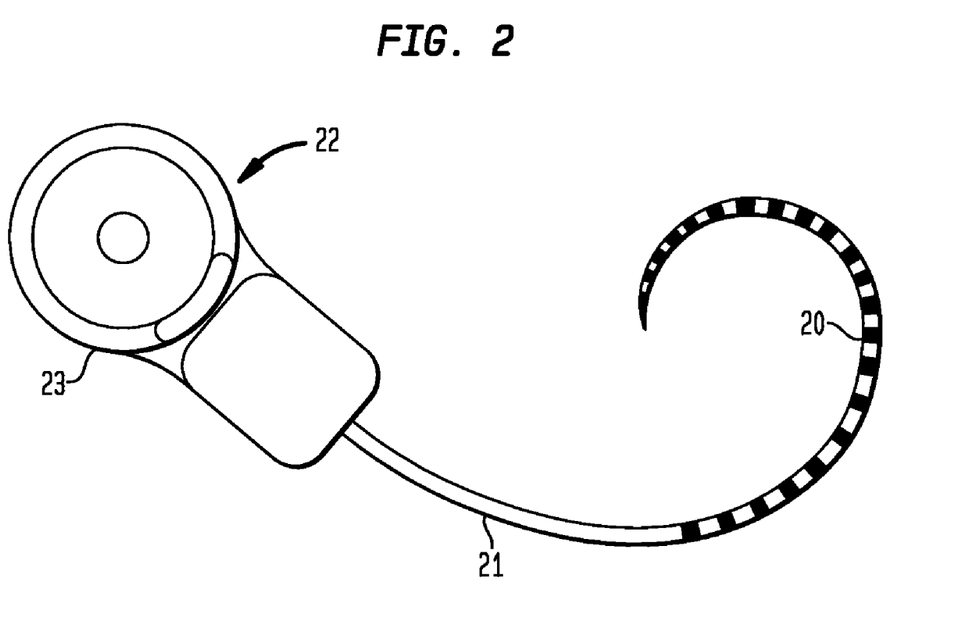
FIG. 2 depicts an implantable component of a hearing implant system.

Embodiments of a hearing implant are depicted in FIGS. 1 and 2. While for the purposes of this description, a Cochlear implant is depicted, it will be appreciated that other devices for stimulating other locations of an implantee can be envisaged and are encompassed within the present application.

The hearing implant of FIG. 1 comprises two main components, namely an external component including an external housing containing a speech processor 29, and an internal component including an implanted receiver and stimulator unit 22. The external component includes a microphone 27. The speech processor 29 is, in this illustration, constructed and arranged so that it can be mounted on and fit behind the outer ear 11. It will be understood that in an alternative version, the housing for the speech processor 29 and/or the microphone 27 may be worn on the body. Attached to the speech processor 29 is an external antenna coil 24 which transmits electrical signals to the implanted unit 22 via a frequency modulated (FM) radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9.

Figure 3A:
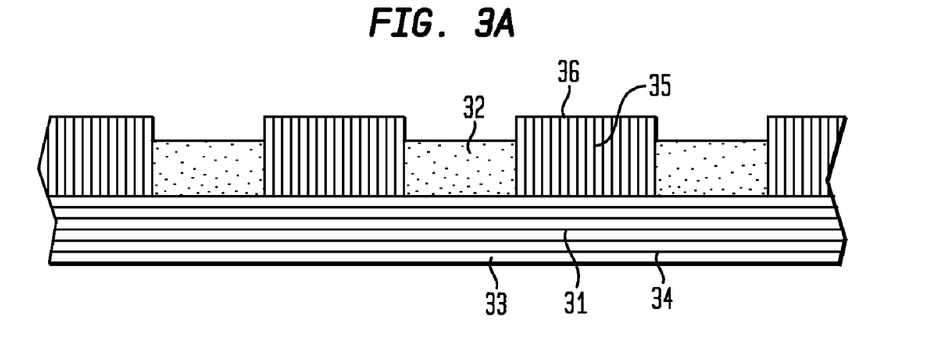
FIGS. 3a-3c depict an electrode array having a surface pattern.
Figure 3B:
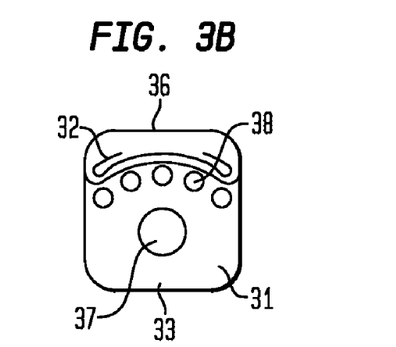
Figure 3C:
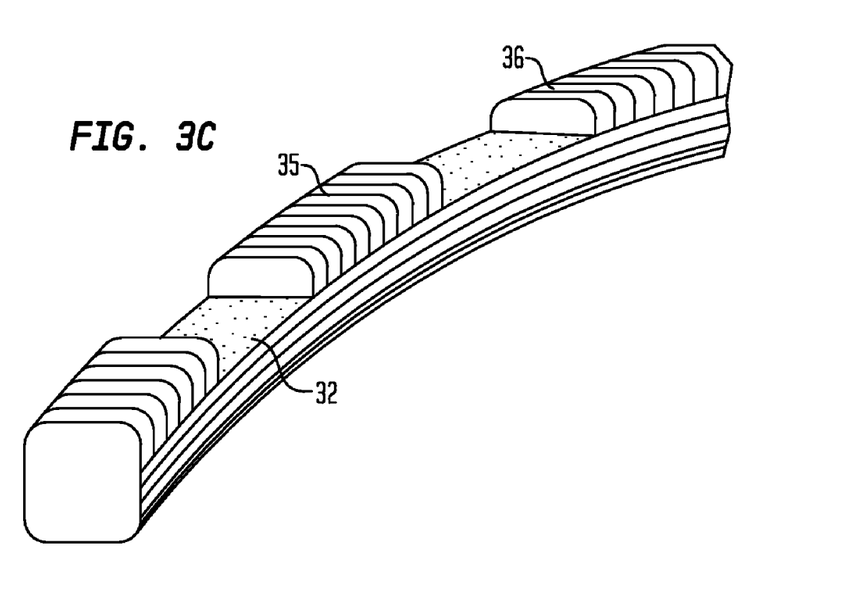

An enlargement of one example of the array 20 is provided in FIGS. 3a to 3c. In this embodiment, the array 20 comprises a series of longitudinally extending platinum half-bend electrodes 32 that are recessed into the silicone elongate body 31. As depicted in FIG. 3b, the array has a lumen 37 and a plurality of wires extending therethrough to the electrodes 32. The surface of the elongate member 31, at least in the location of the electrodes 32, is provided with a series of grooves that are designed to direct any tissue growth that may occur on the array 20 away from the electrodes 32. It is to be understood that the aim of the grooves is not to necessarily prevent tissue growth on the array 20. Rather, the purpose of the grooves is to minimize tissue growth extending over the electrodes 32 and so causing an increase in the impedance of the array 20.

The outer or under surface 33 of the elongate member 31 is provided with a series of parallel longitudinally extending grooves 34. The grooves 34 are designed to facilitate tissue growth along the outer surface of the array 20 and so away from the electrodes 32. This arrangement not only reduces the impedance and related power consumption of the electrodes 32 by reducing the amount fibrous tissue growth on and around the electrodes, but as the arrangement facilitates tissue growth in regions away from the auditory nerve 9, it will increase the impedance in that area and hence direct current away from that area and towards the auditory nerve 9.

As depicted in FIGS. 3a-3c, the inner surface 36 of the array 20 is provided with a series of transverse grooves 35 between each of the electrodes 32. Again, these grooves 35 preferably direct any tissue growth that may occur away from the electrodes 32.

Figure 4:
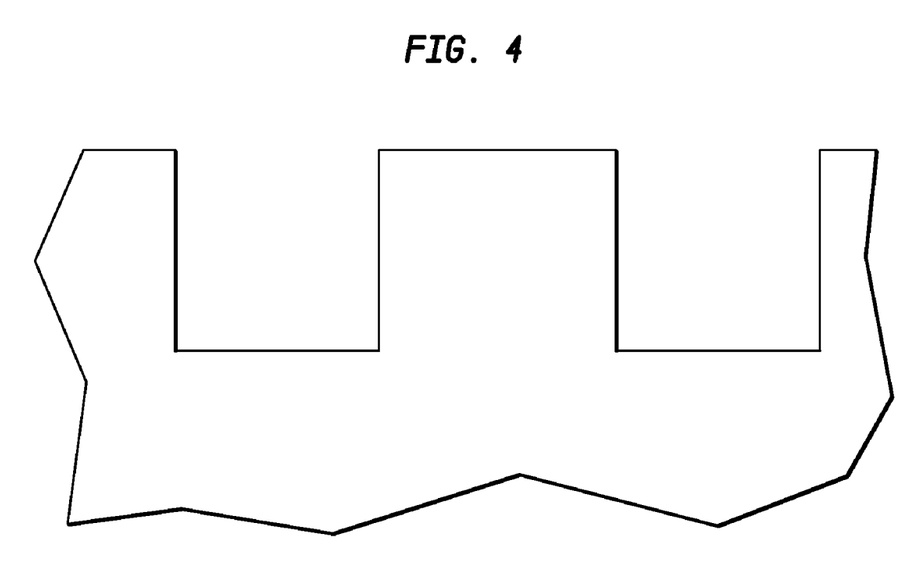
FIG. 4 is a cross-section of one example of a surface pattern.

In the embodiment depicted in FIGS. 3a-3c, the grooves 34 and 35 are parallel and each of identical width, depth and spacing. The grooves (see FIG. 4) are 5 µm deep and have a width and spacing of between 1 and 10 µm. It will be appreciated that other depths, widths and spacings might be utilized. It will be further appreciated that the width, depth and spacing need not be identical for all grooves.

Figure 5A:
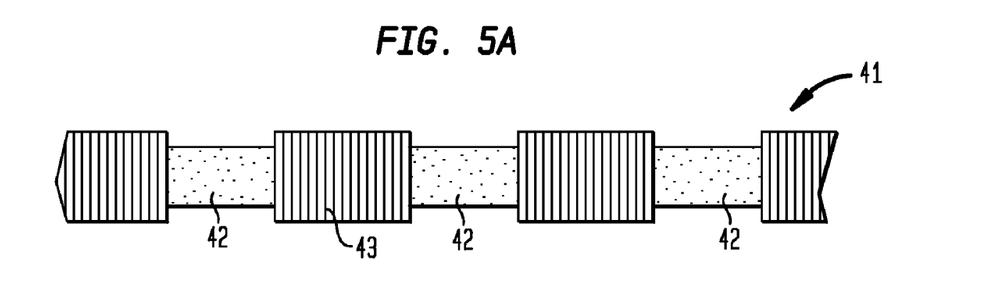
FIGS. 5a-5c depict another example of an electrode array.
Figure 5B:
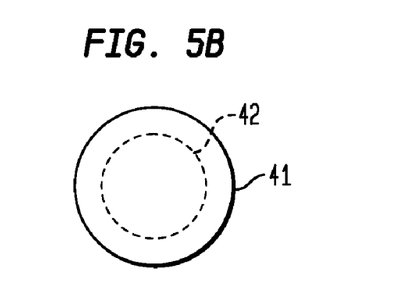
Figure 5C:
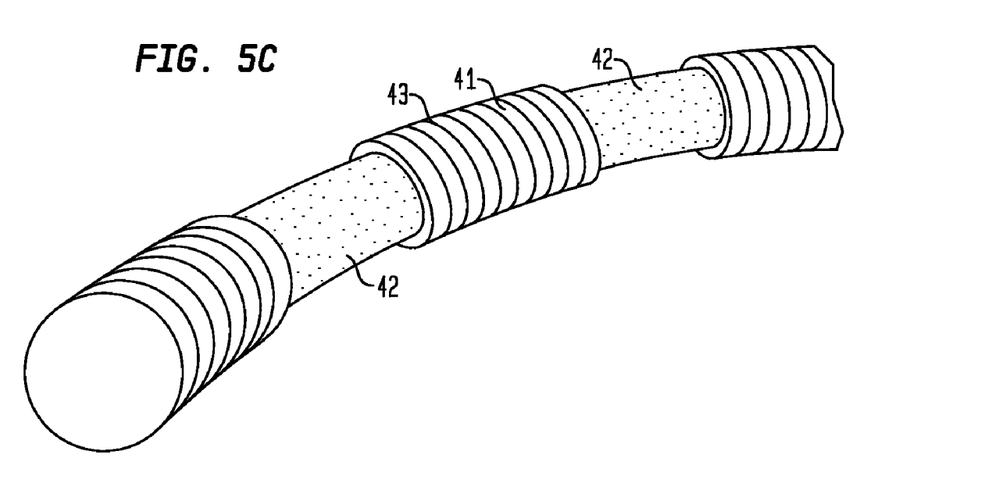

FIGS. 5a-5c depicts an alternative arrangement in which the array 20 comprises a substantially cylindrical silicone elongate member 41 supporting a series of ring electrodes 42. In this arrangement, the surface has a series of annular grooves 43 positioned between each of the electrodes 42. Again, the grooves 43 preferably direct any tissue growth away from the electrodes 42 following implantation of the array 20.

Figure 6:
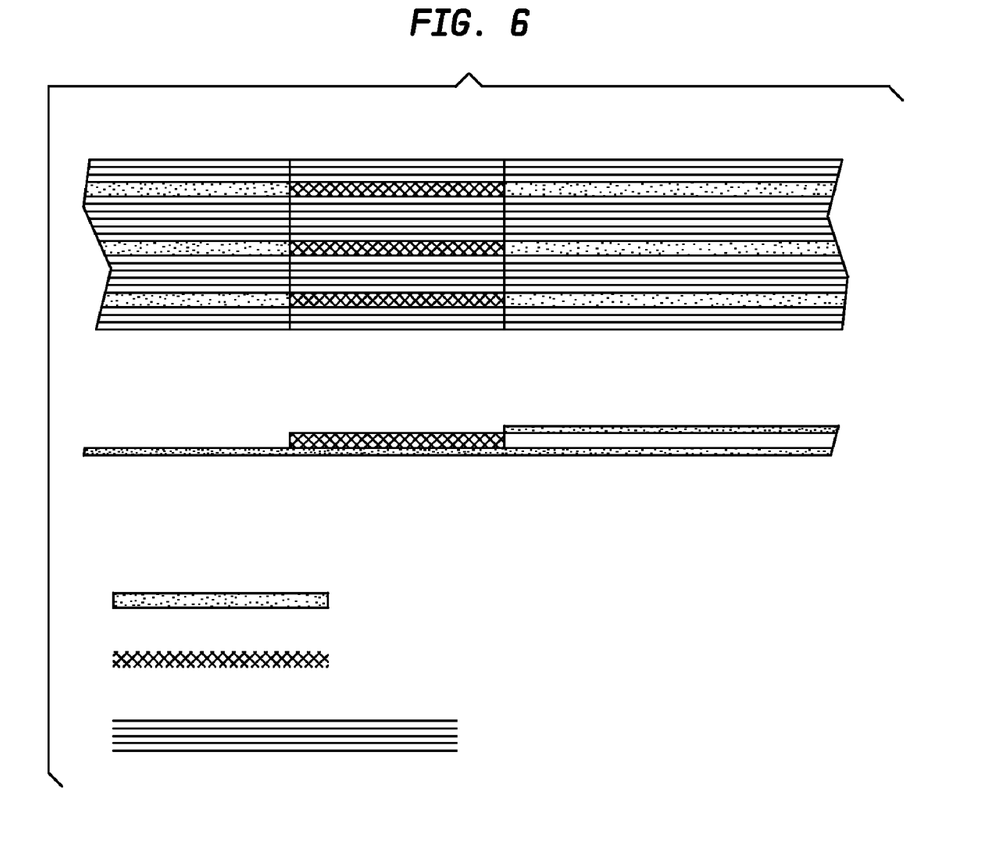
FIG. 6 depicts a still further example of an electrode array.

FIG. 6 depicts an arrangement in which the electrodes are longitudinal. In this embodiment, the grooves are also longitudinal.

Figure 7A:
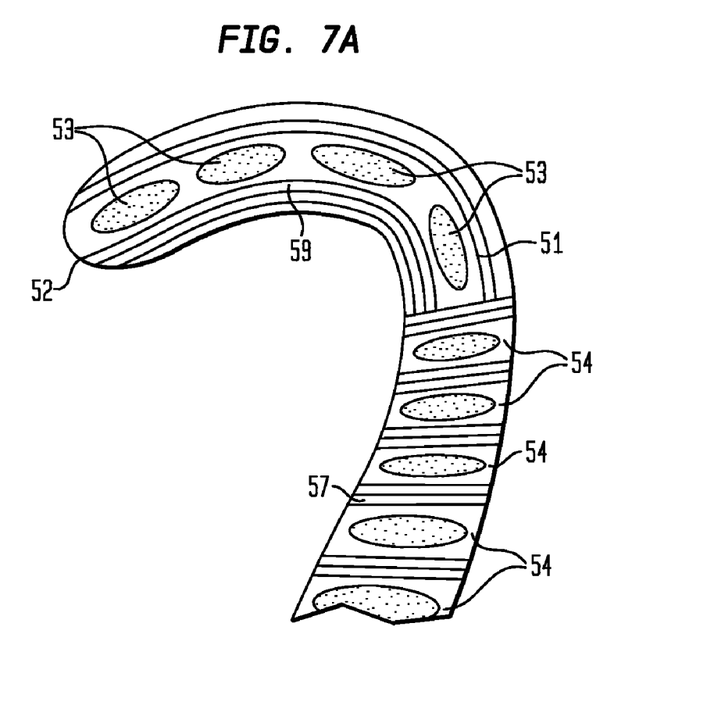
FIGS. 7a and 7b depict yet another example of an electrode array.
Figure 7B:
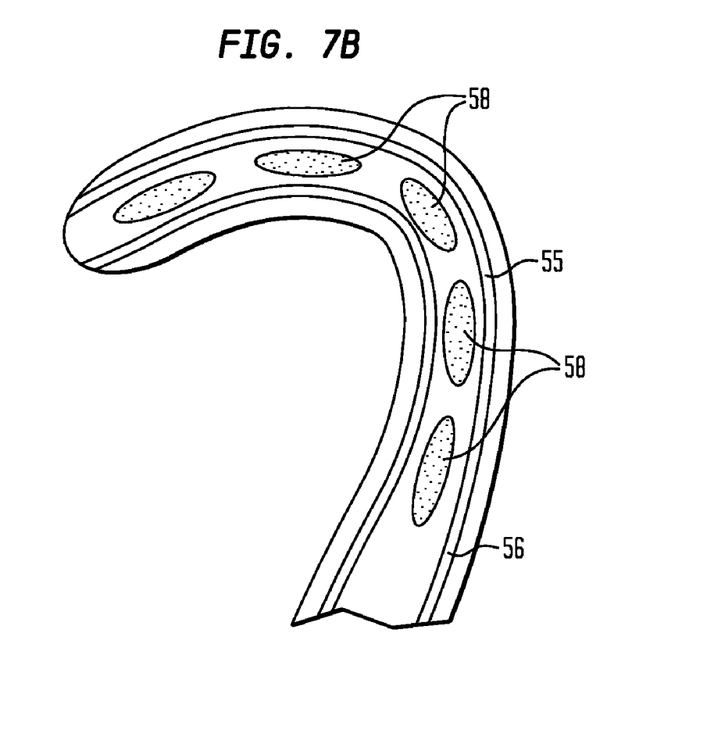

FIGS. 7a and 7b depict an electrode array 20 having an inner surface 51 having 32 electrodes thereon, an outer surface having 17 electrodes supported thereon and two sidewalls. For the sake of clarity, not all of the electrodes are depicted in FIGS. 7a and 7b. On the inner surface 51, the array has 4 longitudinally extending electrodes 53 closest to the distal end 52 while the remaining 28 electrodes 54 extend transversely. The 17 electrodes 58 on the outer surface 55 extend longitudinally. The electrodes on both surfaces of the array are positioned substantially within the plane of the array.

In this arrangement, the outer surface 55 and the sidewalls have a plurality of longitudinally extending grooves 56. On the inner surface 51, a series of transverse grooves 57 are provided between the transverse electrodes 54 and a series of longitudinally extending grooves 59 are provided between the tip electrodes 53. Again, the orientation of the grooves preferably directs any tissue growth that may occur following implantation away from the electrodes of the array.

Other orientations and combinations of orientations of grooves and/or other surface features can be envisaged that are directed to meeting the requirement of minimizing tissue growth over the electrodes of the array. In one embodiment, the surface pattern can comprise an array of relatively small pillars. Such pillars or other surface features may have a height ranging between less than a micron to tens of microns to utilize the properties of cytoskeletal molecules to bond in differing degrees to surface with different surface structures.

The patterned elongate members can be used in conjunction with other techniques to minimize or inhibit tissue growth. Other possible techniques include coating the array, or a portion thereof, with a material that inhibits or promotes organic molecular deposition. In this regard, those regions of the array where tissue growth is unwanted, namely on and around the electrodes, can be coated with an organic growth inhibitor, whilst those regions of the array, such as those regions remote from the electrodes, can be coated with am organic growth promoter to promote tissue growth in these regions.

In this regard, one type of material that tends to promote the adsorption of organic molecules is myosin, a molecule that is attracted to actin. By coating the array with a compound such as myosin in a patterned fashion, as discussed above, the cytoskeletal molecules will be attracted and deposited on the array in a patterned fashion which assists in directing the growth of tissue in the region.

The depicted elongate members can be formed from a suitable biocompatible material. As already described, that material can be a silicone, such as Silastic MDX 4-4210. In another embodiment, the elongate member can be formed from a polyurethane.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An implantable tissue-stimulating hearing implant for an implantee comprising:
    an elongate member having at least one electrode, wherein at least a portion of the surface of the elongate member comprises a plurality of grooves configured to at least partially control tissue growth on and/or around the elongate member, wherein said plurality of grooves are configured to control the tissue growth such that the growth is directed to occur away from the at least one electrode.

2. The hearing implant of claim 1, wherein at least some of the plurality of grooves are substantially parallel with respect to each other.

3. The hearing implant of claim 1, wherein the grooves have substantially the same depth and/or substantially the same width.

4. The hearing implant of claim 1, wherein the grooves have a depth of about 5 μm.

5. The hearing implant of claim 1, wherein the grooves have a width of between approximately 1 μm to approximately 10 μm and are spaced apart by a distance of between approximately 1 μm to approximately 10 μm.

6. The hearing implant of claim 1, wherein the at least one electrode comprises a plurality of electrodes, and wherein at least one of the plurality of electrodes is supported along the inner surface of the elongate member for at least a portion of its length.

7. The hearing implant of claim 6, wherein the plurality of grooves extend longitudinally along the outer surface of the elongate member.

8. The hearing implant of claim 6, wherein the plurality of grooves comprise transverse grooves disposed on the inner surface between at least some of the plurality of electrodes.

9. The hearing implant claim 6, wherein at least one of the plurality of electrodes is supported along the outer surface of the elongate member for at least a portion of its length.

10. The hearing implant of claim 9, wherein at least some of the plurality of electrodes on both the inner surface and the outer surface extend longitudinally, and at least some of the plurality of electrodes on the inner surface extend transversely.

11. The hearing implant of claim 10, wherein the longitudinally extending electrodes on the inner surface are grouped relatively closer toward a distal end of the elongate member than the transversely extending electrodes.

12. The hearing implant of claim 9, wherein the plurality of grooves on the outer surface comprise a plurality of longitudinal grooves.

13. The hearing implant of claim 12, wherein the plurality of grooves comprise transverse grooves disposed between the transversely extending electrodes on the inner surface.

14. The hearing implant of claim 13, wherein the plurality of grooves comprise longitudinally extending grooves disposed adjacent the longitudinally extending electrodes on the inner surface.

15. The hearing implant of claim 1, wherein the elongate member is substantially cylindrical and, wherein the at least one electrode comprises a plurality of ring electrodes.

16. The hearing implant of claim 1, wherein the plurality of grooves comprise annular grooves disposed on the surface of the elongate member between adjacent electrodes.

17. The hearing implant of claim 1, wherein the configuration comprises a deposit of a molecule adsorption promoting material applied to the surface of the elongate member.

18. The hearing implant of claim 17, wherein the molecule adsorption promoting material is myosin.

19. The hearing implant of claim 18, wherein the molecule absorption promoting material is deposited in a plurality of parallel lines on the surface of the elongate member.

20. An implantable tissue-stimulating hearing implant for an implantee comprising:
an elongate member having at least one electrode, at least a portion of the surface of the elongate member comprising a plurality of grooves configured to at least partially control tissue growth on and/or around the elongate member, the surface further comprising a coating of a molecule adsorption promoting material deposited on the portion of the surface that at least partially controls tissue growth on and/or around the elongate member, wherein the plurality of grooves are configured to control the tissue growth such that the growth is directed to occur away from the at least one electrode.

21. The hearing implant of claim 20, wherein the elongate member has an inner surface and an outer surface, a plurality of electrodes being supported along the inner surface of the elongate member for at least a portion of its length and wherein the plurality of grooves are configured to extend longitudinally along the outer surface of the elongate member.

22. The hearing implant of claim 21, wherein a plurality of transverse grooves are present on the inner surface between at least some of the electrodes.

23. The hearing implant of claim 20, wherein the elongate member is substantially cylindrical and wherein the at least on electrode comprises a plurality of ring electrodes.

24. The hearing implant of claim 21, wherein the surface of the elongate member comprises a pattern comprising a plurality of annular grooves in the elongate member between each of the electrodes.

25. The hearing implant of claim 21, wherein at least some of the electrodes on both the inner surface and the outer surface extend longitudinally and at least some of the electrodes on the inner surface extend transversely.

26. The hearing implant of claim 25, wherein the longitudinally extending electrodes on the inner surface are grouped relatively closer to a distal end of the elongate member than the transversely extending electrodes.

27. The hearing implant of claim 20, wherein the molecule adsorption promoting material is myosin.

28. An implantable tissue-stimulating hearing implant for an implantee comprising:
an elongate member having at least one electrode, at least a portion of the surface of the elongate member comprising a plurality of grooves configured to at least partially control tissue growth on and/or around the elongate member, the portion of the surface of the elongate member further having a coating of a molecule adsorption promoting material that assists in at least partially controlling tissue growth on and/or around the elongate member, wherein the plurality of grooves are configured to control the tissue growth such that the growth is directed to occur away from the at least one electrode.

29. The hearing implant of claim 28, wherein at least some of the plurality of grooves are substantially parallel with respect to each other.

30. The hearing implant of claim 28, wherein each of the grooves has substantially the same depth and/or width.

31. The hearing implant of claim 28, wherein the grooves have a depth of about 5 μm.

32. The hearing implant of claim 28, wherein the grooves have a width of between approximately 1 μm to approximately 10 μm and are spaced apart by a distance of between approximately 1 μm to approximately 10 μm.

* * * * *